(12) United States Patent
Carman

(10) Patent No.: US 6,521,601 B1
(45) Date of Patent: Feb. 18, 2003

(54) METHOD AND COMPOSITION FOR INHIBITION OF VIRAL REPLICATION

(75) Inventor: Mark D. Carman, San Mateo, CA (US)

(73) Assignee: Signal Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 07/868,539

(22) Filed: Apr. 14, 1992

(51) Int. Cl.[7] ..................... A01N 43/04; A61K 31/7052
(52) U.S. Cl. ..................... 514/44; 536/23.1; 536/23.72; 536/24.1; 536/24.2; 435/91.1; 435/235.1; 435/236; 435/238; 435/240.2; 435/320.1
(58) Field of Search ........................... 514/44; 536/23.1, 536/23.72, 24.1, 24.2; 435/91.1, 235.1, 236, 238, 948, 974, 240.2, 320.11; 935/6, 7, 8, 10, 32; 430/91.33

(56) References Cited

U.S. PATENT DOCUMENTS

| | | | |
|---|---|---|---|
| 4,689,320 A | * 8/1987 | Kaji ............................. | 514/44 |
| 5,070,012 A | 12/1991 | Nolan et al. .................... | 435/6 |
| 5,142,047 A | * 8/1992 | Summerton et al. ........ | 544/118 |
| 5,208,149 A | * 5/1993 | Inouye ......................... | 435/91 |

OTHER PUBLICATIONS

Wagner, R. W., 1994, Nature 372: 333–335.*
Stein et al., 1993, Science 261: 1004–1012.*
Gura, T., 1995, Science 270: 575–577.*
Stull et al., 1995, Pharmaceutical Research 12(4): 465–483.*
Sakata et al. 1990 Nuc. Acids Res. 18(13): 3831–3839.*
Metzler, D. E. 1977 in: *Biochemistry*. The Chemical Reactions of Living Cells, Academic Press, p. 103.*
Uhlmann et al.. 1990 Chemcial Reviews, 90(4): 544–584).x.*
Snedecor etal. 1989. in: *Statistical Method*. Eighth Edition, Iowa State Univ. Press, Ames, Iowa, pp. 10–13, 26–37, and 64–68.*
Mitsuya etal. 1990. Science. 249, 1533–1544.*
Nester etal. (1978) in: *Microbiology*. Second Edition Holt, Rinehart & Winston, New York, p. 170.*
Bielinska, A., et al., "Regulation of Gene Expression with Double–Stranded Phosphorothioate Oligonucleotides," Science 250:997–1000 (1990).
Bogerd, H.P., et al., "The type I human T–cell leukemia virus (HTLV–I) Rex trans–activator binds directly to the HTLV–I Rex and the type 1 human immunodeficiency virus Rev RNA response elements," Proc. Natl. Acad. Sci. USA 88:5704–5708 (1991).
Chang, Y–N., et al., "The Epstein–Barr Virus Zta Transactivator: a Member of the bZIP Family with Unique DNA–Binding Specificity and a Dimerization Domain That Lacks the Characteristic Heptad .Leucine Zipper Motif," J. Virol. 64(7):3358–3369 (1990).
Cullen, B.R., and Greene, W.C., "Regulatory Pathways Governing HIV–1 Replication," Cell 58:423–426 (1989).
Everett, R.D., et al., "The major transcriptional regulatory protein of herpes simplex virus type 1 includes a protease resistant DNA binding domain," Nucleic Acids Res. 18(15):4579–4585 (1990).
Everett, R.D., et al., "Purification of the DNA binding domain of herpes simplex virus type 1 immediate–early protein Vmw175 as a homodimer and extensive mutagenesis of its DNA recognition site," Nucleic Acids Res. 19 (18): 4901–4908 (1991).
Garcia, J.A., et al., "Functional domains required for tat–induced transcriptional activation of the HIV–1 long terminal repeat," EMBO J. 7(10):3143–3147 (1988).
Grinnell, B.W., and Wagner, R.R., "Inhibition of DNA–Dependent Transcription by the Leader RNA of Vesicular Stomatitis Virus: Role of Specific Nucleotide Sequences and Cell Protein Binding," Mol. & Cell. Biol. 5(10):2502–2513 (1985).
Harel–Bellan, A., et al., "In situ detection of a heat–shock regulatory element binding protein using a soluble short synthetic enhancer sequence," Nucleic Acids Res. 17(1 ):4077–4087 (1989).
Helene, C., "Control of gene expression by oligonucleotides covalently linked to intercalating agents," Genome 31:413–421 (1989).
Jones, N., "Complex Inhibitions: Inhibitions of gene transcription by protein–protein interactions between activators and inhibitors may be a widespread form of regulation." Current Biol. 1(4):224–226 (1991).
Kornberg, R.D., and Lorch, Y., "Irresistible Force Meets Immovable Object: Transcription and the Nucleosome," Cell 67:833–836 (1991).
Kristie, T.M., and Roizman, B., "α4, the major regulatory protein of herpes simplex virus type 1, is stably and specifically associated with promoter–regulatory domains of α genes and of selected other viral genes," Proc. Natl. Acad. Sci. USA 83:3218–3222 (1986).
Morch, M.D., et al., "A new 'sense' RNA approach to block viral RNA replication in vitro," Nucleic Acids Res. 15(10):4123–4130 (1987).
Sullenger, B.A., et al., "Overexpression of TAR Sequences Renders Cells Resistant to Human Immunodeficiency Virus Replication," Cell 63:601–608 (1990).

\* cited by examiner

*Primary Examiner*—Christopher S. F. Low
(74) *Attorney, Agent, or Firm*—Pennie & Edmonds LLP

(57) ABSTRACT

A method and pharmaceutical composition for inhibiting viral replication in infected cells are described. The pharmaceutical composition includes a DNA fragment which has covalently linked strands. The DNA fragment contains a 6–30 basepair region whose sequence corresponds to that of a regulatory element in a virus. The method includes introducing a fragment into the cell in an amount sufficient to inhibit replication of the virus in the cell.

10 Claims, 2 Drawing Sheets

| VIRUS | REGULATORY ELEMENT SEQUENCE |
|---|---|
| EBV R protein | GTGCCNNNNNNNGTGGAC |
| papilloma E2 | ACCGNNNNCGGT |
| E12 | GGCAGGTGG |
| MLTF | CACGTGACCG |
| VSV leader | ATTATTAtcatta |
| tax | TGACG(T/A) |
| Zta | tTG(A/T)GCAAttt |
| Vaccinia | AAAAATTGAAA(A/T)CTA |

Fig. 4

METHOD AND COMPOSITION FOR INHIBITION OF VIRAL REPLICATION

FIELD OF THE INVENTION

The present invention relates to a method and pharmaceutical composition for inhibiting viral replication in cells.

REFERENCES

Ausubel, F. M. et al. *Current Protocols in Molecular Biology*, John Wiley and Sons, Media, Pa.

Chang, Y.-N., et al., J. Virology (1990) 7: 3358–3369.

Dartman, K., et al. (1986) Virology 151: 124–130.

Elion, G. B., et al. (1977) Proc. Natl. Acad. Sci USA 74:5617–5620.

Everett, R. D. et al. (1990) Nuc. Acids. Res. 18: 4579–4588.

Gottlieb, M. S., et al., N. Eng. J. Med. 305:425–3 (1981).

Grau, D. R., Visalli, R. V., Brandt, C. R. (1989) Invest. Opthalmol. Vis. Sci. 30: 2474–2480.

Grinnell, B. W., et al. (1989) J. Virol 63: 1604–1611.

Gruffat, H., et al. (1990) NAR 18:6835–43.

Hausheer, F. H. et al. (1990) Anti-Cancer Drug Des. 5: 159–167.

Helene, C. and Thuong, N. T. (1989) Genome 31: 413–421.

Hentosh, P., et al. (1992) Anal. Biochem. 201: 277–281.

Mitsuya, M., et al. (1985) Proc. Natl. Acad. Sci. USA 82: 7096–7100, USA.

Nelson, P. S., et al. (1989) Nuc. Acids Res. 17: 7179–7186.

Ono, A. et al. (1991) Biochem. 30: 9914–9921.

Poteat, H. T., et al., (1989) J. Virol. 63: 1604–1611.

Praseuth, D. (1988) Proc. Natl. Acad. Sci. USA 85: 1349–1353.

Smith, R. A., et al., "Ribavirin: A broad spectrum antiviral agent: In: Stapleton, T., Editor, Studies With a Broad Spectrum Antiviral Agent. International Congress and Symposium Service (London), Royal Society of Medicine, 3–23 (1986).

BACKGROUND OF THE INVENTION

The challenge in developing an effective therapy and prophylaxis for viral disease is to achieve inhibition of viral processes without producing extreme side effects and preferably without inducing viral resistance. Since viral replication requires use of the cellular apparatus of the host, treating virus infection by inhibiting viral replication can be lethal to the infected host cells as well. Ideally, an anti-viral therapeutic would act selectively to inhibit or eliminate some vital part of viral processes, without affecting the host cell.

Currently, the most widely used anti-viral agents are nucleoside analogs. This class of drugs acts by disrupting viral replication, either by inhibiting enzymes required for nucleic acid processing, or by producing a defective viral genome, such as by premature termination of replication. As an example, acyclovir, a purine analog used in treating a variety of viral diseases, including herpes simplex virus-1 (HSV-1) and herpes simplex virus-2 (HSV-2) inhibits viral replication at several key points, including inhibition of viral thymidine kinase and DNA polymerase, and DNA strand elongation (Elion). Ribavirin, another purine analog, is the drug of choice in treating respiratory syncytial viruses (RSV) infection. This compound appears to act by reducing cellular GTP levels, blocking the action of several GTP-dependent viral processes (Smith). A drug used in the treatment of HIV infection is zidovudine (Azidothymidine; AZT), a thymidine analog which is particularly effective against human retroviruses. AZT acts with high affinity to block viral RNA-dependent DNA polymerase (reverse transcriptase); however, it also blocks human DNA-polymerase and causes chain termination (Mitsuya).

Other nucleic acid analogs include ganciclovir, vidarabine, idoxuridine, trifluridine and foscarnet (an inorganic phosphate analog). As indicated above, all of these drugs, by blocking viral replication, also have the capacity to disrupt normal host replication and/or DNA transcription processes as well.

Understanding of the mechanisms of infection and replication of viruses has led to alternate drug therapies, including attempts to block viral entry into cells, alter protein synthesis at the host ribosomes, complexation of viral DNA/RNA, and immunomodulation. Interferons are glycoproteins which have complex actions, including enhancement of certain host immune responses as well as direct antiviral activity. They act to prevent, rather than to treat established viral infection, and their use leads to undesirable problems including acute, serious discomfort, bone marrow suppression, viral resistance, and development of host immune response to the interferon.

Treatment with "anti-sense" polymers of nucleic acids is a method in which the particular viral genome is the select target. The treatment provides a highly discriminating approach which would be expected to have minimal side-effects; its use as a therapeutic is hampered by problems of targeting, introduction into cells, and the quantity of material that would be required to block each strand produced by the virus.

Agents which bind to and interfere with host ribosomal protein synthesis will block viral replication. These include the toxin ricin, various plant proteins such as pokeweed anti-viral protein, alpha sarcin, and other low molecular weight compounds. In general, however, these compounds lack selectivity for viral processes. In the treatment of HIV, an RNA virus, specific inhibition of the unique retroviral enzyme, reverse transcriptase is a therapeutic target. Non-retroviral systems do not produce or use this enzyme.

In some instances, understanding of structural aspects of the mechanisms of replication of viruses has provided additional drug therapies. For example, certain viruses, contain a viral envelope which surrounds the viral capsid and nucleic acid. This envelope can serve as an additional target for therapeutic assault.

SUMMARY OF THE INVENTION

The present invention provides a method of inhibiting replication of a virus in infected cells. The method involves selecting a DNA fragment which contains covalently linked strands and which has 6–30 basepairs and a total size of less than about 100 basepairs. The sequence of the DNA fragment corresponds to that of a regulatory element in the virus. The DNA fragment is introduced into a cell in an amount sufficient to inhibit replication of the virus.

In a preferred embodiment, the two strands of the DNA fragment are linked in a 5' to 3' direction by a nucleotide sequence $X_1X_2X_3X_4$, where $X_1$ is U or T, and $X_2$ is U, T, G, A or C, $X_3$ is C, and $X_4$ is G (SEQ ID NO: 14); or $X_1$ is G, and $X_2$ is U, T, G, A or C, $X_3$ is G or A, and $S_4$ is A (SEQ ID NO: 15); or $X_1$ is C, and $X_2$ is U or T, $X_3$ is U or T, and $X_4$ is G (SEQ ID NO: 16), and where $X_1$ is covalently attached to a 3' terminus of the DNA and $X_4$ is covalently attached to a 5' terminus of the DNA.

In another embodiment, the method includes selecting a DNA fragment which further includes a nucleotide base containing a group-specific reactive moiety capable of covalently bonding to a protein. Preferably, such a reactive moiety is selected from the group consisting of 6-mercaptopurine, 5-bromo-deoxyuridine, 5-formyl-deoxyuridine, 5-hydroxylmethyl-deoxyuridine, 6-azopurine, a 2-halo-purine, and a 5 halo-uridine.

In yet another preferred embodiment, the method of the invention is used to inhibit replication of Herpes Simplex Virus. 1 and the DNA fragment has the sequence SEQ ID NO: 4.

In another aspect, the invention includes a pharmaceutical composition for treating a virus infection. The pharmaceutical composition includes a pharmaceutical excipient containing a DNA fragment, as characterized by covalently linked strands having a 6–30 basepair region whose sequence corresponds to that of a regulatory element in the virus. The fragment has a total size of, less than about 100 base pairs.

In a preferred embodiment, the DNA fragment contained in the pharmaceutical composition includes a nucleotide sequence $X_1 X_2 X_3 X_4$, where $X_1$ is U or T, $X_2$ is U, T, G, A or C, $X_3$ is C, and $X_4$ is G (SEQ ID NO: 14); or $X_1$ is G, $X_2$ is U, T, G, A or C, $X_3$ is G or A, and $X_4$ is A (SEQ ID NO: 15); or $X_1$ is C, and $X_2$ is U or T, and $X_3$ is U or T, and $X_4$ is G (SEQ ID NO: 16), and where, in each case, $X_1$ is covalently attached a 3' terminus of the DNA fragment and $X_4$ is covalently attached to a 5' terminus of the DNA fragment. This nucleotide sequence covalently links the two strands of the DNA fragment at one or both ends, in a 5'-3' direction.

In another embodiment, the pharmaceutical composition further includes an antiviral agent selected from the group consisting of acyclovir, ribavirin, ganciclovir, zidovudine, vidarabine, idoxuridine, trifluridine and foscarnet.

In another preferred embodiment, the DNA fragment of the pharmaceutical composition includes the sequence SEQ ID NO: 4.

BRIEF DESCRIPTION OF THE FIGURES

FIG. 4 shows sequences of oligonucleotide corresponding to one strand of each of various viral specific regulatory elements: EBV R protein (SEQ ID NO:6; Gruffat), papilloma E2 (SEQ ID NO: 7; Dartman), E12 (SEQ ID NO: 8), MLTF (SEQ ID NO: 9; Carthew), VSV leader (SEQ ID NO: 10; Grinnell), tax (SEQ ID NO: 11; Poteat), Zta (SEQ ID NO: 12; Chang), and Vaccinia (SEQ ID NO: 13; Moss), where capital letters A,C,G,T represent conserved bases, the case letters a,c,g,t represent base additions to the regulatory sequence, the presence of which stabilize binding, and the letter N represents any nucleotide substitution.

DETAILED DESCRIPTION OF THE INVENTION

I. Antiviral Activity of Synthetic Regulatory Units

A. Inhibition of Viral Replication in Cells

This section describes methods used to assess DNA fragments useful in the practicing of the method of the invention to inhibit viral infection in cells.

Generally, compounds are tested for inhibition of viral replication or infectivity in cultured cells. As detailed in Example 1, infectivity of Herpes Simplex Virus-1 (HSV-1), a double stranded DNA virus, was examined by incubating mammalian host cells with test oligonucleotide for a specific period of time, generally about 2–24 hr. The culture medium is removed, and the cells are infected with virus. After an absorption period, excess virus is rinsed away, and the cells are given fresh media containing the desired concentration of the test oligonucleotide. Forty-eight hours later, the infected cells are frozen and thawed repeatedly, to release viral particles, the sample is diluted serially and applied to separate wells of cultured cells. The amount of infectious virus present in each well is measured by a viral plaque assay (Example 1C) on host cell monolayers.

Figure 1:
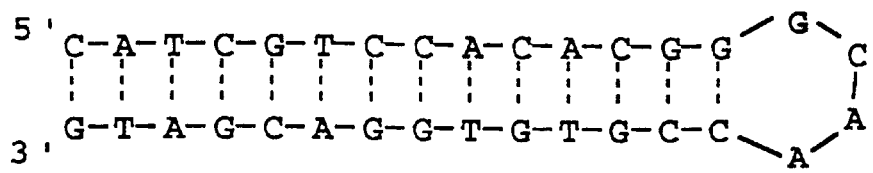
FIG. 1 shows the structure of DNA fragment TP004 (SEQ ID NO: 4)

Table 1 shows the results of incubation of test DNA fragment oligonucleotides with Vero (African Green Monkey Kidney) cells to determine their effects on infectivity by HSV-1 (strain KOS). As shown, treatment of cells with TP004 (SEQ ID NO: 4) resulted in a significant reduction of viral titer at all concentrations tested (0.1–4 $\mu$M). The structure of TP004 is shown in FIG. 1. The double stranded portion of this DNA fragment corresponds to a sequence of DNA recognized by HSV-1 transcription factor VMW 175 (Everett). Test oligonucleotides TP003 (SEQ ID NO: 3), TP005 (SEQ ID NO: 5) and the combination of TP001 (SEQ ID NO: 1) and TP002 (SEQ ID NO: 2), exhibited biphasic effects on viral infectivity of cells.

TABLE 1

| Sample | Concentration | Titer (yield) | % Yield |
| --- | --- | --- | --- |
| Control |  | 2.35 ± 0.35 × 10$^7$ | 100 |
| TP001 + 002* | 4.0 $\mu$M | 2.2 × 10$^7$ | 93.6 |
|  | 1.0 $\mu$M | 1.8 × 10$^7$ | 76.6 |
|  | 0.4 $\mu$M | 1.5 × 10$^7$ | 63.8 |
|  | 0.1 $\mu$M | 1.3 × 10$^7$ | 55.3 |
| TP003 | 4.0 $\mu$M | 2.35 ± 1.2 × 10$^7$ | 100 |
|  | 1.0 $\mu$M | 1.65 ± 0.78 × 10$^7$ | 70.2 |
|  | 0.4 $\mu$M | 0.815 ± 0.26 × 10$^7$ | 34.6 |
|  | 0.1 $\mu$M | 1.3 ± 0.28 × 10$^7$ | 55.3 |
| TP004 | 4.0 $\mu$M | 7.35 × 10$^6$ | 31.3 |
|  | 1.0 $\mu$M | 1.6 ± 0.71 × 10$^7$ | 68.1 |
|  | 0.4 $\mu$M | 1.85 ± 1.48 × 10$^7$ | 78.7 |
|  | 0.1 $\mu$M | 1.5 ± 0.57 × 10$^7$ | 63.8 |
| TP005 | 4.0 $\mu$M | 2.35 ± 0.21 × 10$^7$ | 100 |
|  | 1.0 $\mu$M | 4.1 ± 1.56 × 10$^7$ | 174 |
|  | 0.4 $\mu$M | 2.4 ± 0.57 × 10$^7$ | 102 |
|  | 0.1 $\mu$M | 1.65 ± 0.7 × 10$^7$ | 70.2 |

*Titers were not determined in duplicate. All other titers were determined from duplicate samples.

II. DNA Fragments

This section describes the structures and synthesis of DNA fragments useful in practicing the present invention.

A. Structures

Figure 2:
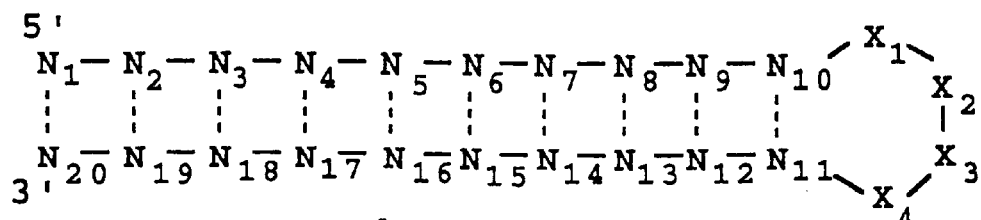
FIG. 2 shows a generalized structure of a double-stranded DNA fragment having nucleotide sequence $X_1 X_2 X_3 X_4$ linking the two strands (SEQ ID NO: 17)

A schematic diagram of an antiviral double stranded DNA fragment constructed in accordance with the invention is shown in FIG. 2. In the figure, N indicates a deoxyribonucleotide base (A,C,G,U, or T). It can be seen that the DNA fragment is composed primarily of a double stranded stretch of DNA, preferably about 6–30 base pairs in length. The complementary strands forming the majority of the DNA fragment are hydrogen bonded as indicated by the dotted lines to form the structure shown. In one embodiment, illustrated in FIG. 3, the 6–30 basepair sequence may be repeated a number of times, with such repeated sequences attached one to another directly, or through a filler sequence, F, which may be one or a plurality of nucleotide bases, or any covalent linker which does not interfere with the ability of the DNA fragment complementary regions to form hydrogen bonds.

With continued reference to FIG. 2, it is seen that the two strands of the oligonucleotide are preferably covalently bonded one to another, to enhance stability of the double stranded structure. In FIG. 2, the covalent bonding is effected by the presence of a tetraoligonucleotide, or tetraloop, sequence connecting the 3' terminus of one strand of the DNA to the 5' terminus of the complementary strand of the DNA. In accordance with the invention, the tetraloop has one of three preferred sequences to provide stability to the molecule. With reference to the notation shown in FIG. 2, these preferred sequences are as follows: (i) $X_1$ is U or T, $X_2$ is U, T, G, A or C, and $X_3$ is C, and $X_4$ is G (SEQ ID NO: 14); (ii) $X_1$ is G, and $X_2$ is U, T, G, A or C, $X_3$ is G or A, and $X_4$ is A (SEQ ID NO: 15); and (iii) $X_1$ is C, $X_2$ is U or T, $X_3$ is U or T, and $X_4$ is G (SEQ ID NO: 16). As shown, $X_1$ is covalently attached to a 3' terminus of the DNA and $X_4$ is covalently attached to the 3' terminus of the DNA. It can appreciated that such a tetraoligonucleotide can be attached at either or both ends of the double stranded oligonucleotide.

It can further be appreciated, that covalent bonding between the two strands can be formed by incorporation into the sequence a number of modifying groups, known in the art, effective to stabilize the double strand configuration of the oligonucleotide. One such group is an amidate linker group (Ono). In another example, the strands can be photo crosslinked by incorporation of a cross-linking reagent, such as a p-azidophenacyl group, into one of the strands, by methods known in the art (Praseuth).

Double-stranded oligonucleotides of the invention may be formed having normal phosphodiester backbones common to native DNA molecules, or preferably, to provide additional desirable properties to the structures, such molecules may contain alternate synthetic backbones. One such preferable backbone structure is a thiodiester backbone, in which a sulfur group replaces one or both of the oxygen moieties present in the conventional nucleotide phosphodiester bond. This substitution may provide the features of enhanced stability and cell permeability. Alternatively, the structure may contain methylphosphonate groups in the 5'-3' internucleotide bonds of the oligonucleotide (Hausheer). Other possible configurations include, but are not restricted to, a anomeric conformations of oligonucleotides. It is appreciated that any backbone conformation is compatible with the DNA fragment, as long as such backbone does not perturb the ability of the double strand nucleotide region to interact with a viral transcription factor.

Figure 3A:
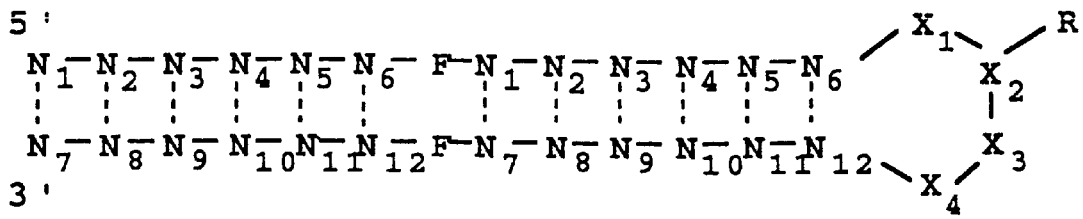
FIG. 3A shows a DNA fragment having multiple copies of a regulatory element sequence N1–N6, with complementary sequence $N_7-N_{12}$ and linked by nucleotide sequence $X_1 X_2 X_3 X_4$ and having a functional group, R, capable of covalently attaching to a transcription factor protein (SEQ ID NO: 18)
Figure 3B:
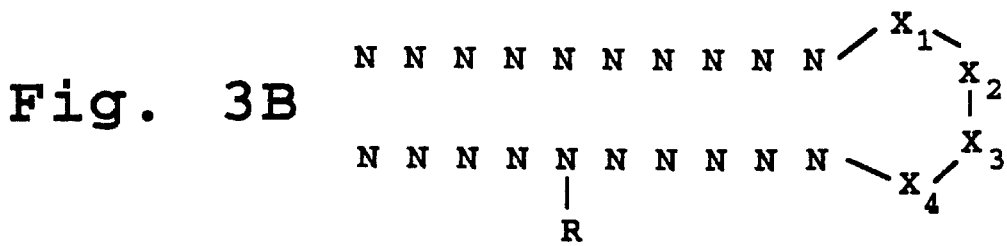
FIG. 3B shows a DNA fragment having a functional group R within the complementary sequence of the fragment (SEQ ID NO: 19)
Figure 3C:
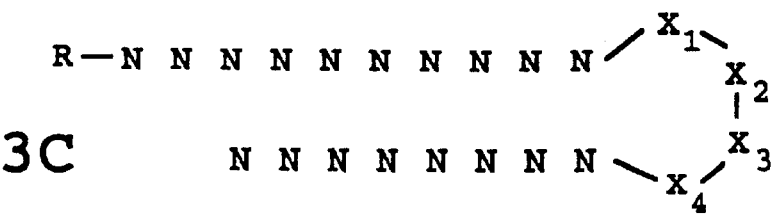
FIG. 3C shows a DNA fragment having a functional group R at a terminus of the DNA fragment (SEQ ID NO: 20)

FIGS. 3 (A–C) show a schematic diagrams of DNA fragments of the invention having a reactive group, R, attached at various positions within the DNA fragment, including position 2 of the tetranucleotide joining group (3A), at a-position within the complementary region or within a filler sequence region of the DNA fragment (3B), and at a terminus of the DNA fragment (3C). Such a reactive group is effective to bind covalently to a protein contacted by the DNA fragment, when the protein and DNA fragment are in binding proximity, one to another. Such reactive groups may be attached to an existing base of the oligonucleotide, as through a 5-phosphoramidite modification (Nelson), or in a preferred embodiment, when the group is an activated nucleotide group, it may preferably be incorporated into the oligonucleotide sequence, as by using PCR reaction (Hentosh). Exemplary reactive groups which are activated nucleotides suitable for these purposes include 6'-mercaptopurine, 5-bromo-deoxyuridine, 5-formyl-deoxyuridine, 5-hydroxylmethyl-deoxyuridine, and 6-azopurine. Other activated nucleotides include 2 halopurines, exemplified by 2-fluoro-guanosine or 2-chloro-adenosine, and 5-halo-uridines, such as 5-fluoro-deoxyuridine.

B. Synthesis

DNA fragment oligonucleotides of the invention may be prepared using conventional chemical oligonucleotide synthetic techniques, and, particularly, such fragments can be synthesized as a single oligonucleotide sequence containing complementary regions such as regions $N_1$–$N_{10}$ and $N_{11}$–$N_{20}$ shown in FIG. 2. Under annealing conditions detailed in Example 2, and particularly when such regions are separated in the linear sequence by a non-complementary oligonucleotide sequence such as the tetranucleotide sequence shown, such complementary regions hydrogen bond to form the double stranded DNA fragment shown. Conformation and annealment of oligonucleotides is verified by heating of solutions containing the oligonucleotides at 80° C. for 10 minutes, followed by slow cooling to room temperature.

DNA fragments of the invention may also be prepared by other techniques known in the art including amplification by polymerase chain reaction (PCR) of an appropriate template or cloning in a standard expression vector system followed by purification by size fractionation (Ausubel).

III. Method of Inhibiting Viral Replication

This section describes the selection of antiviral DNA fragments and their use in the treatment of viral infections.

A. Selection of Antiviral DNA Fragments

In accordance with the invention, in order to treat a specific viral infection, a DNA fragment is selected whose sequence corresponds to that of a regulatory element in the virus to be treated. Exemplary viral regulatory elements are shown as single strand sequences in FIG. 4. The DNA fragment preferably has a 6–30 double stranded basepair region corresponding to such a regulatory element sequence and total size of less than about 100 base pairs. A schematic diagram of an antiviral DNA fragment is shown in FIG. 2. The DNA fragment is synthesized, as described in Example 2, preferably as a linear sequence having complementary regions, joined by a linking oligonucleotide sequence $X_1X_2X_3X_4$, where $X_1$ is U or T, $X_2$ is U, T, G, A or C, $X_3$ is C, $X_4$ is G (SEQ ID NO: 14); or $X_1$ is G, $X_2$ is U, T, G, A or C, $X_3$ is G or A, and $X_4$ is A (SEQ ID NO: 15); or $X_1$ is C, $X_2$ is U or T, $X_3$ is U or T, and $X_4$ is G (SEQ ID NO: 16), and where $X_1$ is covalently attached to a 3' terminus of the DNA double strand region and $X_4$ is covalently attached to a 5' terminus of the DNA double strand region, as shown in FIG. 2. DNA fragment TP004 shown in FIG. 1 is exemplary of such a DNA fragment which is synthesized as a linear oligonucleotide having complementary regions linked by a tetraoligonucleotide sequence, then subjected to annealing conditions, detailed in Example 2.

Selection of sequences to be synthesized was made based on consensus the sequence of a regulatory element in the virus. TP004 (FIG. 1) is based on the regulatory element recognized by a virally encoded transcriptional regulatory protein of HSV-1, termed Vmw 175 (Everett). Additional viral targets and their regulatory elements sequences are listed in FIG. 4.

DNA fragments are selected for anti-viral activity against the appropriate virus, as exemplified by HSV virus, detailed in Example 1. DNA fragments showing significant antiviral activity in such an assay are used to produce pharmaceutical compositions of the invention.

B. In vivo Antiviral Activity of DNA Fragments

DNA fragments selected as described above are prepared in a pharmaceutical composition in an appropriate pharmaceutical excipient, and administered to a subject, as described in Example 3. Exemplary routes of administration include, but are not limited to, topical or transdermal, intravenous or intraarterial, and nasal insufflation. Other known antiviral agents, such as acyclovir, ribavirin, ganciclovir, zidovudine, vidarabine, idoxuridine, trifluridine and foscarnet may be combined with the antiviral DNA fragments of the invention to provide enhanced anti-viral activity.

The following examples illustrate, but in no way are intended to limit the present invention.

Materials

All chemicals were obtained from Aldrich (St. Louis, Mo.) unless otherwise indicated. Culture media were obtained from Gibco (Grand Island, N.Y.).

High titer viral stocks (HSV-1 KOS) were obtained from ATCC.

Vero cells (ATCC) were grown and maintained in culture, as described by Grau.

EXAMPLE 1

In Vitro Antiviral Activity Assays

A. Test Agents

Each test oligonucleotide was suspended in TE buffer (10 mM Tris pH. 7.5, 1 mM EDTA) at a concentration of 4 mM.

B. Viral Yield Reduction Assay

Vero (African Green Monkey Kidney) cells were plated in 24 well tissue culture plates ($1\times10^5$ cells per well) and were incubated overnight at 37° C. Medium (1 ml per well) was then removed and replaced with fresh medium (DME+5% calf serum) containing the appropriate concentration of test oligonucleotide. Oligonucleotide concentrations of 25.0 $\mu$M, 10.0 $\mu$M, 4.0 $\mu$M, 1.0 $\mu$M, and 0.1 $\mu$M were tested. Cells were incubated in the presence of the test oligonucleotide for 24 hr. The media was then removed, and the cells were infected with HSV-1 strain KOS at a multiplicity of infection (MOI) of 2.0 pfu per cell. After an adsorption period of 1 hr, excess virus was rinsed away, and the cells were given fresh media (DME+2% serum) containing the desired concentration of the test oligonucleotide. Forty-eight hours later, the infected cells were frozen and thawed 3 times (−80° C. to 37° C.), diluted serially 10-fold in DME+2% serum, and the amount of infectious virus present in each well measured by plaque assay on Vero cell monolayers, as described below. Control cultures were infected but not treated with drugs.

C. Virus Plaque Assay

Vero cells were grown to confluency in 24-well plates in culture, as described above. Infected cell extracts, from part B above, were diluted in sterile PBS, and applied (0.1 ml/well) as serial dilutions to the wells. The plates were incubated for 1 hour at 37° for viral adsorption. Following the incubation, the excess virus was washed from the cells, by three sterile PBS rinses, and the plates were overlaid with soft agar containing media. After three days, the cultures were stained, and plaques were counted.

The percent yield was calculated using the formula:

yield from treated cells/yield from control cells×100

Results of in vitro viral reduction assay of HSV-1 strain KOS are shown in Table 1.

EXAMPLE 2

Preparation of Oligonucleotides

A. Synthesis

Oligonucleotides were prepared in an ABI DNA synthesizer (Applied Biosystems, Foster City, Calif.) using the conditions described in the operating manual. Fragments were synthesized either as single strands having complementary regions and allowed to self-anneal, or synthesized as two strands, as detailed below.

TP001 and TP002

TP001 and TP002 are complementary strands. TP001 is an 18 mer having the sequence: SEQ ID NO.: 1 (ATCGTCATCGTCATCGTC) and a molecular weight (MW) of 5764. TP002 is an 18 mer having the sequence SEQ ID NO: 2 (GACGATGACGATGACGAT), MW=5971. TP001 and TP002 are complementary sequences which were mixed and annealed at 56 C. for 30 min, then allowed to cool to RT.

TP003

TP003 is a 40-mer having the sequence SEQ ID NO: 3 (ATCGTCATCGTCATCGTCGCAAGACGATGACGATGACGAT) and MW=13117. This sequence contains complementary regions comprising the first 18, and last 18 nucleotide bases. It was self-annealed at 56° for 30 min, then allowed to cool to room temperature and used alone.

TP004

TP004 is a 32 mer having the sequence SEQ ID NO: 4 (CATCGTCCACACGGGCAACCGTGTGGACGATG) and MW=10437. This sequence contains complementary regions comprising the first 14, and last 14 nucleotide bases. It was self-annealed at 56° for 30 min, then allowed to cool to room temperature and used alone.

TP005

TP005 is 32-mer having the sequence SEQ ID NO: 5 (GTAGCAGGTGTGCCAACGGGCACACCTGCTAC) and MW=10437. This sequence contains complementary regions comprising the first 14, and last 14 nucleotide bases. It was self-annealed at 56° for 30 min, then allowed to cool to room temperature and used alone.

B. Verification of structure

Conformation and annealment of oligonucleotides was verified by heating of solutions containing the oligonucleotides at 80° C. for 10 minutes, followed by slow cooling to room temperature.

EXAMPLE 3

In Vivo Antiviral Activity Assays

Mice. NIH/OLA inbred mice are obtained originally from Jackson Labs and are used at 8 weeks of age, any with abnormal eyes are rejected.

Inoculation. Mice are anesthetized by intraperitoneal injection of sodium pentobarbitone and inoculated by scarification of the left cornea with a 26-gauge needle through 5 μl drop of medium containing $10^4$ plaque forming units (PFU) HSV type 1 (HSV-1) strain McKrae. Control mice are inoculated in the same way with a preparation of uninfected Vero cells made in a similar manner to the virus inoculum (mock inoculum).

Examination of eyes and isolation of virus from eyewashings. Mice are anaesthetized and the cornea, iris and lids examined for signs of disease using a slit lamp microscope. Eyewashings are put onto Vero cells for the isolation of virus (Tullo).

Detection of latent infection. Mice are killed with an overdose of sodium pentobarbitone and the following tissues are removed from the left side: the three parts of the trigeminal ganglion (TG) and the superior cervical ganglion (SCG). The TG is divided in situ so that part 1 (TG1) contains all the ophthalmic and some of the maxillary neurons, part 2 (TG2) contains maxillary neurons and part 3 (TG3), mandibular neurons. The SCG and the parts of TG are each placed in 0.5 ml of medium and incubated at 37° C. in 5% $CO_2$ for 5 days. The tissues are then ground and 50 μl of the suspension is put onto Vero cell monolayers. These are incubated at 37° C. for 2 days before being fixed and stained so that plaques could be identified.

Reactivation of latent infection. At least 40 days after corneal inoculation mice are given 5 mg of cyclophosphamide intravenously in 0.2 ml of phosphate-buffered saline (PBS). One day later, 0.2 mg of dexamethasone in 0.2 ml PBS is injected via the same route. In all experiments except one, mice are anaesthetized immediately after this injection and are held for 90 s with the left eye proptosed, below a Hanovia lamp so that the cornea and lids can be irradiated. The lamp emits a peak of 4.03 $mJ/cm^2$.s at 320 nm. This irradiation produces mild erythema in the skin of the pinna of these mice.

Detection of virus reactivated in vivo.

(i) Isolation of infectious virus from tissues. The three parts of the left TG and the left SCG are each ground in 0.5 ml of medium, then frozen and thawed three times to disrupt all the cells. The resulting cell-free suspensions are put onto a monolayer of Vero cells in 25 $cm^2$ flasks and incubated at 37° C. in 5% $CO_2$. Cultures are examined daily for c.p.e. for 5 days. The upper and lower lids from each mouse are ground together in 0.5 ml of medium, frozen and thawed three times and the resulting cell-free suspensions are put onto a monolayer of Vero cells as above. These cultures are examined for c.p.e. for up to 21 days.

(ii) Detection of virus antigens by peroxidase-antiperoxidase (PAP) staining. Mice are killed with an overdose of sodium pentobarbitone, followed by the removal of the left eye and the lids (or part of the lids). Flat mounts of the corneal epithelium and of the remainder of the eye (the corneal stroma and endothelium, the uvea and sclera, referred to as "globe") are prepared and stained by the PAP method for the detection of HSV-1 antigens, as described by Dyson et al. (1987). Upper and lower lipids were treated separately or selected diseased areas of lids were fixed in Bouin's fluid for 30 min to 1 h and then immersed in 70% ethanol for at least 24 h. They are then embedded in paraffin wax and serial 5 μm sections are cut for PAP staining.

While the invention has been described with reference to specific methods and embodiments, it will be appreciated that various modifications and changes may be made without departing from the invention.

---

It is claimed:

1. A method of inhibiting replication of a virus in an infected cell in vivo, comprising selecting a DNA fragment having (i) a first region having 6–30 bases whose sequence corresponds to a sequence of DNA recognized by a viral-specific transcription factor, (ii) a second region having a sequence of nucleotides complementary to said first region, when said first and second regions are positioned in an anti-parallel configuration, and (iii) joining said first and said second regions in a 5' to 3' direction, a tetranucleotide sequence $X_1X_2X_3X_4$, where $X_1$ is U or T, and $X_2$ is U, T, G, A or C, and $X_3$ is C, and $X_4$ is G (SEQ ID NO: 14); or $X_1$ is G, and $X_2$ is U, T, G, A or C, and $X_3$ is G or A, and $X_4$ is A (SEQ ID NO: 15); or $X_1$ is C, and $X_2$ is U or T, and $X_3$ is U or T, and $X_4$ is G (SEQ ID NO: 16), and introducing the fragment into the cell in an amount sufficient to inhibit replication of the virus in the cell.

2. The method of claim 1, wherein the DNA fragment further includes a nucleotide base containing a group-specific reactive group moiety which covalently binds to a protein.

3. The method of claim 2, wherein the reactive moiety is selected from the group consisting of 6-mercaptopurine, 5-bromo-deoxyuridine, 5-formyl-deoxyuridine, 5-hydroxylmethyl-deoxyuridine, and 6-azopurine, a 2 halo-purine, and a 5-halo-uridine.

4. The method of claim 1, wherein the virus is Herpes Simplex Virus 1 and the DNA fragment has the sequence SEQ ID NO: 4.

5. A pharmaceutical composition for treating a virus infection, comprising a pharmaceutical excipient containing a DNA fragment having (i) a first region having a 5' terminus and a 3' terminus, said region having 6–30 bases whose sequence corresponds to a sequence of DNA recognized by a viral-specific transcription factor, (ii) a second region having a 5' terminus and a 3' terminus, said region having a sequence of nucleotides complementary to said first region when said first and second regions are positioned in an anti-parallel configuration, and (iii) a covalent link between the 5' terminus of one region and the 3' terminus of the other region.

6. The pharmaceutical composition of claim 5, wherein the covalent link is formed in a 5' to 3' direction by a nucleotide sequence $X_1X_2X_3X_4$, where $X_1$ is U or T, $X_2$ is U, T, G, A or C, $X_3$ is C, and $X_4$ is G (SEQ ID NO: 14); or $X_1$ is G, $X_2$ is U, T, G, A or C, $X_3$ is G or A, and $X_4$ is A (SEQ ID NO: 15); or $X_1$ is C, $X_2$ is U or T, $X_3$ is U or T, and $X_4$ is G (SEQ ID NO: 16), and where $X_1$ is covalently attached to a 3' terminus of one region and $X_4$ is covalently attached to a 5' terminus of the other region.

7. The pharmaceutical composition of claim 5, wherein the DNA fragment further includes a nucleotide base containing a group-specific reactive group moiety which covalently binds to a protein.

8. The pharmaceutical composition of claim 5, wherein the reactive moiety is selected from the group consisting of 6-mercaptopurine, 5-bromo-deoxyuridine, 5-formyl-deoxyuridine, 5-hydroxylmethyl-deoxyuridine, and 6-azopurine, a 2 halo-purine, and a 5-halo-uridine.

9. The pharmaceutical composition of claim 5 which further includes an antiviral agent selected from the group consisting of acyclovir, ribavirin, ganciclovir, zidovudine, vidarabine, idoxuridine, trifluridine and foscarnet.

10. The pharmaceutical composition of claim 5, wherein the DNA fragment includes the sequence SEQ ID NO: 4.

* * * * *

SEQUENCE LISTING

<160> NUMBER OF SEQ ID NOS: 20

<210> SEQ ID NO 1
<211> LENGTH: 18
<212> TYPE: DNA
<213> ORGANISM: herpes simplex virus

<400> SEQUENCE: 1
atcgtcatcg tcatcgtc                                          18

<210> SEQ ID NO 2
<211> LENGTH: 18
<212> TYPE: DNA
<213> ORGANISM: herpes simplex virus

<400> SEQUENCE: 2
gacgatgacg atgacgat                                          18

<210> SEQ ID NO 3
<211> LENGTH: 40
<212> TYPE: DNA
<213> ORGANISM: herpes simplex virus

<400> SEQUENCE: 3
atcgtcatcg tcatcgtcgc aagacgatga cgatgacgat                  40

-continued

```
<210> SEQ ID NO 4
<211> LENGTH: 32
<212> TYPE: DNA
<213> ORGANISM: herpes simplex virus

<400> SEQUENCE: 4
catcgtccac acgggcaacc gtgtggacga tg                              32

<210> SEQ ID NO 5
<211> LENGTH: 32
<212> TYPE: DNA
<213> ORGANISM: herpes simplex virus

<400> SEQUENCE: 5
gtagcaggtg tgccaacggg cacacctgct ac                              32

<210> SEQ ID NO 6
<211> LENGTH: 18
<212> TYPE: DNA
<213> ORGANISM: herpes simplex virus
<220> FEATURE:
<221> NAME/KEY: misc_feature
<222> LOCATION: (6)..(12)
<223> OTHER INFORMATION: n = a, t, g, or c

<400> SEQUENCE: 6
gtgccnnnnn nngtggac                                              18

<210> SEQ ID NO 7
<211> LENGTH: 12
<212> TYPE: DNA
<213> ORGANISM: herpes simplex virus
<220> FEATURE:
<221> NAME/KEY: misc_feature
<222> LOCATION: (5)..(8)
<223> OTHER INFORMATION: n = a, t, g, or c

<400> SEQUENCE: 7
accgnnnncg gt                                                    12

<210> SEQ ID NO 8
<211> LENGTH: 9
<212> TYPE: DNA
<213> ORGANISM: herpes simplex virus

<400> SEQUENCE: 8 ggcaggtgg                                                         9

<210> SEQ ID NO 9
<211> LENGTH: 10
<212> TYPE: DNA
<213> ORGANISM: herpes simplex virus

<400> SEQUENCE: 9
cacgtgaccg                                                       10

<210> SEQ ID NO 10
<211> LENGTH: 13
<212> TYPE: DNA
<213> ORGANISM: herpes simplex virus

<400> SEQUENCE: 10
attattatca tta                                                   13

<210> SEQ ID NO 11
```

-continued

```
<211> LENGTH: 6
<212> TYPE: DNA
<213> ORGANISM: herpes simplex virus
<220> FEATURE:
<221> NAME/KEY: misc_feature
<222> LOCATION: (6)..(6)
<223> OTHER INFORMATION: n = t or a

<400> SEQUENCE: 11 tgacgn                                                                      6

<210> SEQ ID NO 12
<211> LENGTH: 11
<212> TYPE: DNA
<213> ORGANISM: herpes simplex virus
<220> FEATURE:
<221> NAME/KEY: misc_feature
<222> LOCATION: (4)..(4)
<223> OTHER INFORMATION: n = a or t

<400> SEQUENCE: 12
ttgngcaatt t                                                               11

<210> SEQ ID NO 13
<211> LENGTH: 15
<212> TYPE: DNA
<213> ORGANISM: herpes simplex virus
<220> FEATURE:
<221> NAME/KEY: misc_feature
<222> LOCATION: (12)..(12)
<223> OTHER INFORMATION: n = a or t

<400> SEQUENCE: 13
aaaaattgaa ancta                                                           15

<210> SEQ ID NO 14
<211> LENGTH: 4
<212> TYPE: DNA
<213> ORGANISM: herpes simplex virus
<220> FEATURE:
<221> NAME/KEY: misc_feature
<222> LOCATION: (1)..(1)
<223> OTHER INFORMATION: n = u or t
<220> FEATURE:
<221> NAME/KEY: misc_feature
<222> LOCATION: (2)..(2)
<223> OTHER INFORMATION: n = u, t, g, a, or c

<400> SEQUENCE: 14 nncg                                                                        4

<210> SEQ ID NO 15
<211> LENGTH: 4
<212> TYPE: DNA
<213> ORGANISM: herpes simplex virus
<220> FEATURE:
<221> NAME/KEY: misc_feature
<222> LOCATION: (2)..(2)
<223> OTHER INFORMATION: n = u, t, g or a
<220> FEATURE:
<221> NAME/KEY: misc_feature
<222> LOCATION: (3)..(3)
<223> OTHER INFORMATION: n = g or a

<400> SEQUENCE: 15 gnna                                                                        4

<210> SEQ ID NO 16
<211> LENGTH: 4
```

```
<212> TYPE: DNA
<213> ORGANISM: herpes simplex virus
<220> FEATURE:
<221> NAME/KEY: misc_feature
<222> LOCATION: (2)..(2)
<223> OTHER INFORMATION: n = u or t
<220> FEATURE:
<221> NAME/KEY: misc_feature
<222> LOCATION: (3)..(3)
<223> OTHER INFORMATION: n = u or t

<400> SEQUENCE: 16 cnng                                                                    4

<210> SEQ ID NO 17
<211> LENGTH: 24
<212> TYPE: DNA
<213> ORGANISM: herpes simplex virus
<220> FEATURE:
<221> NAME/KEY: misc_feature
<222> LOCATION: (1)..(10)
<223> OTHER INFORMATION: n = any nucleotide
<220> FEATURE:
<221> NAME/KEY: misc_feature
<222> LOCATION: (15)..(24)
<223> OTHER INFORMATION: n = any nucleotide
<220> FEATURE:
<221> NAME/KEY: misc_feature
<222> LOCATION: (11)..(14)
<223> OTHER INFORMATION: Sequence from position 11 to position 14 can be
      either the sequence of SEQ ID NO. 14, 15 or 16

<400> SEQUENCE: 17
nnnnnnnnnn nnnnnnnnnn nnnn                                             24

<210> SEQ ID NO 18
<211> LENGTH: 25
<212> TYPE: DNA
<213> ORGANISM: herpes simplex virus
<220> FEATURE:
<221> NAME/KEY: misc_feature
<222> LOCATION: (7)..(7)
<223> OTHER INFORMATION: n = filler sequence
<220> FEATURE:
<221> NAME/KEY: misc_feature
<222> LOCATION: (8)..(8)
<223> OTHER INFORMATION: n = any nucleotide, but the same nucleotide as
      position 1
<220> FEATURE:
<221> NAME/KEY: misc_feature
<222> LOCATION: (9)..(9)
<223> OTHER INFORMATION: n = any nucleotide, but the same nucleotide as
      position 2
<220> FEATURE:
<221> NAME/KEY: misc_feature
<222> LOCATION: (10)..(10)
<223> OTHER INFORMATION: n = any nucleotide, but the same nucleotide as
      position 3
<220> FEATURE:
<221> NAME/KEY: misc_feature
<222> LOCATION: (11)..(11)
<223> OTHER INFORMATION: n = any nucleotide, but the same nucleotide as
      position 4
<220> FEATURE:
<221> NAME/KEY: misc_feature
<222> LOCATION: (12)..(12)
<223> OTHER INFORMATION: n = any nucleotide, but the same nucleotide as
      position 5
<220> FEATURE:
<221> NAME/KEY: misc_feature
<222> LOCATION: (13)..(13)
<223> OTHER INFORMATION: n = any nucleotide, but the same nucleotide as
      position 6
<220> FEATURE:
<221> NAME/KEY: misc_feature
```

```
<222> LOCATION: (25)..(25)
<223> OTHER INFORMATION: n = any nucleotide, but the same nucleotide as
      position 18
<220> FEATURE:
<221> NAME/KEY: misc_feature
<222> LOCATION: (24)..(24)
<223> OTHER INFORMATION: n = filler sequence
<220> FEATURE:
<221> NAME/KEY: misc_feature
<222> LOCATION: (18)..(23)
<223> OTHER INFORMATION: n = any nucleotide
<220> FEATURE:
<221> NAME/KEY: misc_feature
<222> LOCATION: (26)..(26)
<223> OTHER INFORMATION: n = any nucleotide, but the same nucleotide as
      position 19
<220> FEATURE:
<221> NAME/KEY: misc_feature
<222> LOCATION: (27)..(27)
<223> OTHER INFORMATION: n = any nucleotide, but the same nucleotide as
      position 20
<220> FEATURE:
<221> NAME/KEY: misc_feature
<222> LOCATION: (28)..(28)
<223> OTHER INFORMATION: n = any nucleotide, but the same nucleotide as
      position 21
<220> FEATURE:
<221> NAME/KEY: misc_feature
<222> LOCATION: (29)..(29)
<223> OTHER INFORMATION: n = any nucleotide, but the same nucleotide as
      position 22
<220> FEATURE:
<221> NAME/KEY: misc_feature
<222> LOCATION: (30)..(30)
<223> OTHER INFORMATION: n = any nucleotide, but the same nucleotide as
      position 23
<220> FEATURE:
<221> NAME/KEY: misc_feature
<222> LOCATION: (14)..(17)
<223> OTHER INFORMATION: Sequence from position 14 to position 17 can be
      either the sequence of SEQ ID NO. 14, 15 or 16
<220> FEATURE:
<221> NAME/KEY: misc_feature
<222> LOCATION: (15)..(15)
<223> OTHER INFORMATION: n is attached to a functional group "R",
      capable of covalently attaching to a transcription factor protein
<220> FEATURE:
<221> NAME/KEY: misc_feature
<222> LOCATION: (1)..(6)
<223> OTHER INFORMATION: n = any nucleotide

<400> SEQUENCE: 18
nnnnnnnnnn nnnnnnnnnn nnnnn                                     25

<210> SEQ ID NO 19
<211> LENGTH: 24
<212> TYPE: DNA
<213> ORGANISM: herpes simplex virus
<220> FEATURE:
<221> NAME/KEY: misc_feature
<222> LOCATION: (20)..(20)
<223> OTHER INFORMATION: n is attached to a functional group "R",
      capable of covalently attaching to a transcription factor protein
<220> FEATURE:
<221> NAME/KEY: misc_feature
<222> LOCATION: (11)..(14)
<223> OTHER INFORMATION: Sequence from position 11 to position 14 can be
      either the sequence of SEQ ID NO. 14, 15 or 16
<220> FEATURE:
<221> NAME/KEY: misc_feature
<222> LOCATION: (15)..(24)
<223> OTHER INFORMATION: n = any nucleotide
<220> FEATURE:
<221> NAME/KEY: misc_feature
<222> LOCATION: (1)..(10)
<223> OTHER INFORMATION: n = any nucleotide
```

-continued

```
<400> SEQUENCE: 19
nnnnnnnnnn nnnnnnnnnn nnnn                                              24

<210> SEQ ID NO 20
<211> LENGTH: 22
<212> TYPE: DNA
<213> ORGANISM: herpes simplex virus
<220> FEATURE:
<221> NAME/KEY: misc_feature
<222> LOCATION: (1)..(1)
<223> OTHER INFORMATION: n is attached to a functional group "R",
      capable of covalently attaching to a transcription factor protein
<220> FEATURE:
<221> NAME/KEY: misc_feature
<222> LOCATION: (1)..(10)
<223> OTHER INFORMATION: n = any nucleotide
<220> FEATURE:
<221> NAME/KEY: misc_feature
<222> LOCATION: (11)..(14)
<223> OTHER INFORMATION: Sequence from position 11 to position 14 can be
      either the sequence of SEQ ID NO. 14, 15 or 16
<220> FEATURE:
<221> NAME/KEY: misc_feature
<222> LOCATION: (15)..(22)
<223> OTHER INFORMATION: n = any nucleotide

<400> SEQUENCE: 20
nnnnnnnnnn nnnnnnnnnn nn                                                22
```